United States Patent [19]

Bitar et al.

[11] Patent Number: 5,049,279

[45] Date of Patent: Sep. 17, 1991

[54] SELECTIVE EXTRACTION OF AMINO ACIDS

[75] Inventors: Marie-Christine Bitar, Levallois-Perret; Jean-Louis Sabot, Maisons-Laffitte; Paul Aviron-Viollet, Saint-Genis Laval, all of France

[73] Assignee: Rhone-Poulenc Chimie, Courbevoie, France

[21] Appl. No.: 348,074

[22] Filed: May 5, 1989

Related U.S. Application Data

[63] Continuation of Ser. No. 66,107, Jun. 25, 1987, abandoned.

[30] Foreign Application Priority Data

Jun. 25, 1986 [FR] France .............................. 86 09410

[51] Int. Cl.$^5$ .......................................... B01D 11/04
[52] U.S. Cl. ..................................... 210/634; 210/511
[58] Field of Search ................ 426/657, 44, 656, 555, 426/537; 210/634, 511; 260/705; 424/70, 72, 71

[56] References Cited

U.S. PATENT DOCUMENTS

| | | | |
|---|---|---|---|
| 2,894,954 | 7/1959 | Dewitt et al. .................. | 260/705 X |
| 3,912,822 | 10/1975 | Yokotsuka et al. .................. | 426/44 |
| 3,970,614 | 7/1976 | Goodwin ........................ | 426/555 X |

*Primary Examiner*—Frank Spear
*Attorney, Agent, or Firm*—Burns, Doane, Swecker & Mathis

[57] ABSTRACT

Desired amino acids, e.g., phenylalanine, arginine, leucine, isoleucine, valine and/or histidine, are selectively countercurrently extracted from more complex, essentially cystine-free solutions of a plurality of amino acids, utilizing an organic phosphorus acid extractant, advantageously in solution in at least one alcohol, ether, ketone and/or aliphatic hydrocarbon.

13 Claims, 2 Drawing Sheets

SELECTIVE EXTRACTION OF AMINO ACIDS

This application is a continuation of application Ser. No. 07/066,107, filed Jun. 25, 1987, now abandoned.

BACKGROUND OF THE INVENTION

1. Field of the Invention

The present invention relates to the separation of amino acids from a mixture of at least two amino acids, and, more especially, to the production of amino acids from protein hydrolysates.

2. Description of the Prior Art

A number of different techniques are known to this art for the production of amino acids, the most common of which entail chemical or biochemical syntheses. These techniques generally provide a single amino acid in solution in the medium of preparation. Extraction of such single amino acid and the purification thereof are typically feasible on an industrial scale.

At the present time, however, certain of the amino acids can be produced industrially only with difficulty, and only by chemical methods or fermentation.

All of the amino acids exist as units of peptides and proteins and are components of all life forms, whether vegetable or animal. Attempts have therefore been made to hydrolyze such proteins to extract therefrom the different amino acids. In proteinaceous materials, the amino acids are intermixed in large numbers, on the order of approximately 20.

Various methods have been attempted to separate these amino acids. It will be appreciated that all of the amino acids have physico-chemical properties which differ rather slightly and that in living matter they are all present together, frequently without a truly major component, which further exasperates the difficulty of their separation.

Among the separation techniques proposed in the literature, the following have been reported: precipitation, but here the efficiency of the separation is mediocre and the need to recover the precipitating reagent complicates the process; ion exchange processes which are difficult to carry out in view of the large size of the columns, the strong dilution of the solution and sequential mode of operation of the columns.

It too is known, from U.S. Pat. No. 2,894,954, to separate the amino acids selectively from acid solutions of amino acids, using an aliphatic alcohol solution, but the extraction capacity of the solvent remains low and, while this disadvantage has been partially overcome by the addition of hexylamine, the selectivity remains too weak.

None of the processes of the prior art enable the cost-effective separation of individual natural amino acids from mixtures of amino acids, notably the most commercially attractive of such amino acids, specifically arginine, phenylalanine, leucine, isoleucine, valine and histidine.

SUMMARY OF THE INVENTION

Accordingly, a major object of the present invention is the provision of improved process for the separation of amino acids.

Briefly, the present invention features separation of the amino acids by countercurrently selectively extracting a mixture of at least two amino acids, depleted in cystine values, utilizing an organic phosphorus acid extractant, advantageously in solution in at least one alcohol, ketone, ether and/or at least one hydrocarbon.

DETAILED DESCRIPTION OF THE PREFERRED EMBODIMENTS OF THE INVENTION

Figure 1:
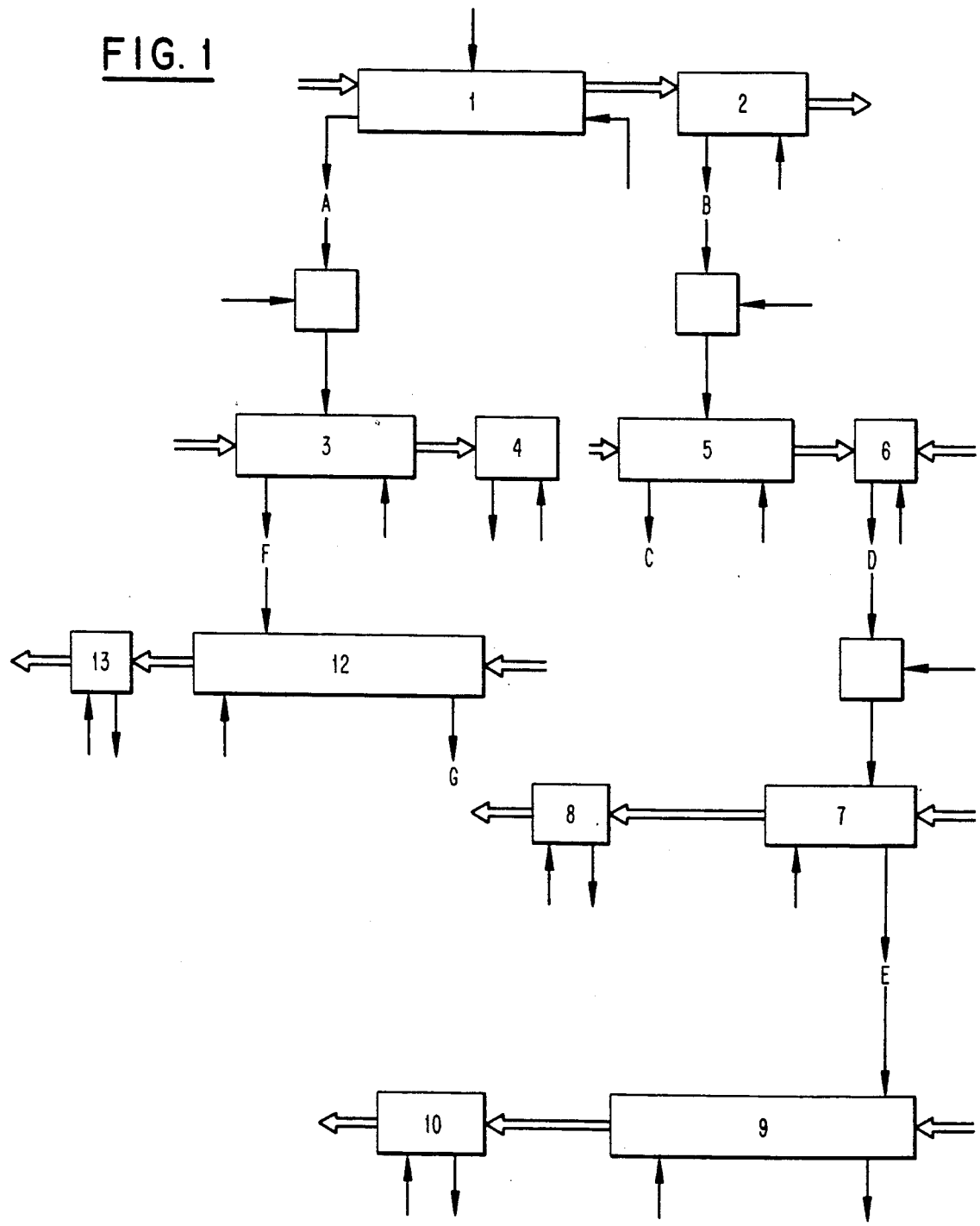
FIG. 1 is a schematic/diagrammatic illustration of one embodiment of apparatus/process according to this invention.

More particularly according to the present invention, the beginning mixtures of amino acids may be widely diverse in origin: biochemical, chemical syntheses, protein hydrolysates, bioconversion products. The proteins used in the present invention may themselves emanate from highly disparate sources: keratin, agriculture, animal, hemoglobin, etc.

The protein hydrolysate preferably treated according to this invention is advantageously a hydrolysate of various keratin wastes, such as hair, wool, feathers, horns, hooves, etc. The hydrolysis is carried out, for example, by means of strong mineral acids, such as sulfuric or hydrochloric acid, strong bases such as sodium or potassium hydroxide and enzymes, for variable periods of time, in particular 6 to 24 hours, and variable temperatures, preferably at about 100° C., specifically for chemical hydrolyses. The aqueous acid solution produced is concentrated, if necessary, either before or after the elimination of the cystine, in particular by precipitation at a higher pH using, for example, sodium hydroxide.

The resulting mixture of at least two amino acids, preferably produced by the hydrolysis of proteins, contains at least 100 g/l amino acids. A concentration greater than 200 g/l is preferred.

This acid solution is countercurrently contacted with an organic solution extractant including an organic phosphorus acid, a linear or branched chain aliphatic alcohol preferably containing from 6 to 14 carbon atoms, and even more preferably 8 to 10 carbon atoms, and/or an aliphatic hydrocarbon.

The organic phosphorus acid is selected from among the dialkylphosphoric, dialkylphosphonic, dialkylphosphinic, diarylphosphoric, diarylphosphonic or diarylphosphinic acids. In particular, it is preferred to use 2-diethylhexylphosphoric acid.

The dialkyl or diarylphosphoric acids advantageously have the following general formula (I):

wherein $R_1$ and $R_2$ are aromatic and/or aliphatic hydrocarbon radicals having from 1 to 18 carbon atoms and in which at least one R group contains from 4 to 15 carbon atoms.

The dialkyl or diarylphosphonic acids advantageously have the following general formula (II):

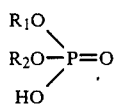

wherein $R_1$ and $R_2$ are as defined above.

The dialkyl or diarylphosphinic acids advantageously have the following general formula (III):

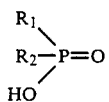

wherein $R_1$ and $R_2$ are also as defined above.

The alcohols, ketones and ethers optionally included are advantageously compounds containing at least 5 carbon atoms.

It is preferred to use a linear or branched chain aliphatic alcohol containing from 8 to 10 carbon atoms and more particularly 2-ethylhexanol.

The optional hydrocarbons are advantageously selected from among the diluents of organic phosphorus acids immiscible with water, such as linear or branched chain aliphatic hydrocarbons containing at least five carbon atoms, aromatic hydrocarbons, halogenated hydrocarbons, and the like. Mixtures of these may also be used, in particular petroleum fractions such as kerosene or of the Solvesso type.

It is preferred to use kerosene, and even more preferably a mixture of alcohol and kerosene.

An especially preferred extraction solvent in the process of the invention has the following composition by volume:
(i) 2-diethylhexylphosphoric acid, 40–80%;
(ii) 2-ethylhexanol, 5–20%; and
(iii) kerosene, 55–0%.

The principal amino acids currently in demand in the marketplace, i.e., valine, leucine, isoleucine, phenylalanine, arginine and histidine are specifically extracted from, the solution of protein hydrolysate depleted of cystine by the following extraction technique:

(a) Phenylalanine is extracted using a quaternary ammonium salt at pH 10 from an amino acid solution in a sulfuric medium. Among the quaternary ammonium salts, the quaternary ammonium chlorides or sulfates corresponding to the formula $R_3N^+ CH_3 Cl^-$ or $(R_3N^+ CH_3)_2 SO_4$, in which R is a hydrocarbon radical having 8 to 10 carbon atoms, are representative. The materials are commercially available under the trademarks Adogen 464 and Aliquat 336. They are preferably used in solution in Solvesso, in a concentration of 3 to 20% by weight;

(b) Arginine is separated by a double extraction using the aforesaid extraction solvents, at pH 2.7 and 7;

(c) Leucine is extracted using the extraction solvents at pH 3;

(d) Isoleucine is separated from a solution of the amino acids depleted in phenylalanine values using the extraction solvents at pH 3.

In order to further illustrate the present invention and the advantages thereof, the following specific examples are given, it being understood that same are intended only as illustrative and in nowise limitative.

EXAMPLE 1

Amino acids were separated from a hydrolysate of feathers, depleted in cystine, which at pH 2.7 had the following composition:
(i) Leucine 21 g/l
(ii) Isoleucine 11.3 g/l
(iii) Phenylalanine 15 g/l
(iv) Arginine 24.5 g/l
(v) Valine 17 g/l
(vi) Serine 39.5 g/l
(vii) Threonine 15 g/l
(viii) Proline 37.6 g/l
(ix) Alanine 15 g/l
(x) Glutamic acid 33.8 g/l
(xi) Aspartic acid 24.5 g/l
(xii) Glycine 26.3 g/l
(xiii) Lysine 5.6 g/l
(xiv) Methionine 1.9 g/l
(xv) Histidine 3.7 g/l
(xvi) NaCl 150 g/l,
a total of 291.7 g/l amino acids.

This solution was contacted with the following extractant solution:
(1) 2-Diethylhexylphosphoric acid 75%
(2) 2-Ethylhexanol 10%
(3) Kerosene 15%

This operation was carried out in the apparatus shown in FIG. 1, in a liquid/liquid extraction battery 1 operating countercurrently and comprising 9 theoretical stages. The solvent was introduced into the battery at stage 1 at a flow rate of 100 ml/hr. The amino acid solution, at pH 2.7, was introduced into the battery at stage 5 at a rate of 100 ml/hr. Selective washing was carried out by the introduction, at stage 9, of an 80 g/l sodium chloride solution in $10^{-3}N$ hydrochloric acid, at a rate of 40 ml/hr. The pH of extraction was controlled at pH 2.7 by the addition of 10N sodium hydroxide into the mixers of stages 2 and 5 at a rate of 10 ml/hr.

The depleted aqueous phase B emanating from stage 1 contained:
(i) Arginine 17.5 g/l
(ii) Histidine 2.6 g/l
(iii) Lysine 4 g/l
(iv) Glutamic acid 24.1 g/l
(v) Glycine 18.8 g/l
(vi) Aspartic acid 17.5 g/l
(vii) Serine 28.2 g/l
(viii) Threonine 10.7 g/l
(ix) Alanine 10.7 g/l
(x) Proline 26.8 g/l
(xi) Valine <60 ml/l
(xii) Phenylalanine <50 ml/l
(xiii) Methionine <6 mg/l
(xiv) Leucine <15 mg/l
(xv) Isoleucine <8 mg/l
(xvi) NaCl 100 g/l,
corresponding to a degree of extraction higher than:
99.5% for valine, methionine and phenylalanine;
99.9% for leucine and isoleucine.

The charged solvent exiting the battery 1 was circulated to the battery 2, having three stages, in which the amino acids extracted in aqueous solution were recovered by concurrently contacting the solvent with a 2N hydyrochloric acid solution, at a rate of 25 ml/hr. The resulting aqueous solution A of amino acids had the following composition:
(i) Leucine 84 g/l (ii) Isoleucine 45.2 g/l
(iii) Phenylalamine 60 ml/l
(iv) Valine 68 ml/l
(v) Methionine 7.6 g/l
(vi) Other amino acids <2.4 g/l The solution B of amino acids was introduced continuously, at pH 7 adjusted by the addition of 10N sodium hydroxide, at a rate of 10 ml/hr. The solution obtained had the following composition:
(i) Arginine 16.3 g/l
(ii) Histidine 2.5 g/l
(iii) Lysine 3.7 g/l
(iv) Glutamic acid 22.4 g/l
(v) Glycine 17.5 g/l
(vi) Aspartic acid 16.3 g/l
(vii) Serine 26.3 g/l
(viii) Threonine 10 g/l
(ix) Alanine 10 g/l
(x) Proline 25 g/l
(xi) Other amino acids <0.2 g/l
(xii) NaCl 92 g/l This solution was with the following extractant solution:
(1) 2-Diethylhexylphosphoric acid 75%
(2) 2-Ethylhexanol 10%
(3) Kerosene 15%

This operation was carried out in the apparatus shown in FIG. 1, in a liquid/liquid extraction battery 3 operating countercurrently and comprising 20 theoretical stages. The solvent was introduced into the battery at stage 1, at a rate of 150 ml/hr. The amino acid solution was introduced at stage 7 at a rate of 150 ml/l. Selective washing was carried out using an 80 g/l sodium chloride solution, at a rate of 80 ml/hr. The pH of extraction was controlled at 7 using 10N sodium hydroxide, introduced into the mixers 3 and 7 at rates of 5 ml/hr.

The depleted aqueous phase F emanating from stage 1 contained more than 99% of each of the amino acids lysine, glutamic and aspartic acids, glycine, serine, threonine, praline, alanine, histidine and other amino acids, and less than 150 mg/l arginine, which corresponds to a degree of extraction of arginine greater than 99%. The solution F had the following composition:
(i) Lysine 2.4 g/l
(ii) Glutamic acid 14.5 g/l
(iii) Glycine 11.4 g/l
(iv) Aspartic acid 10.6 g/l
(v) Serine 17.1 g/l
(vi) Threonine 6.5 g/l
(vii) Alanine 6.5 g/l
(viii) Proline 16.2 g/l
(ix) Histidine 1.6 g/l
(x) Other amino acids ≦0.12 g/l
(xi) Arginine ≦0.15 g/l
(xii) NaCl 80 g/l The solvent charged with arginine emanating from the battery 3 was circulated to a battery 4 having three stages, in which the arginine was countercurrently extracted in aqueous solution using a 2N hydrochloric acid solution, at a rate of 25 ml/hr.

The aqueous phase produced was an aqueous acid solution of arginine, 97.8 g/l, containing less than 3 g/l of the other amino acids.

The depleted aqueous phase F was then contacted with the following organic phase:
(1) 2-Diethylhexylphosphoric acid 75%
(2) 2-Ethylhexanol 10%
(3) Kerosene 15%

This operation was carried out in the apparatus illustrated in FIG. 1 in a liquid/liquid extraction battery 12 operating countercurrently and comprising 19 theoretical stages. The aqueous solution F was introduced into the battery at stage 10 at a rate of 230 ml/hr. The extraction solvent was introduced at stage 1 at a rate of 27 ml/hr. Selective washing was carried out using an 0.15N hydrochloric acid solution, introduced at stage 19 at a rate of 88.5 ml/hr. 10N sodium hydroxide was introduced at stage 1 at a rate of 15 ml/hr.

Under these conditions, the depleted aqueous phase G emanating from stage 1 contained less than 25 mg/l histidine and more than 99.9% of each of the other amino acids of the feed solution F. This corresponded to an extraction yield of histidine of 99.9%. The solvent charged with histidine and emanating from stage 19 was circulated into liquid/liquid extraction battery 13 operating countercurrently and comprising 3 theoretical stages, wherein the extracted histidine was recovered in aqueous phase by contact with a 2N hydrochloric acid solution, at a rate of 10 ml/hr. An acid aqueous phase of histidine, 37.5 g/l, was obtained, containing less than 5 mg/l of other amino acids and corresponding to a purity in histidine of at least 99.95%.

The regenerated extract of the first separation, designated A, was recovered and continuously neutralized by the addition of 10N sodium hydroxide, at a rate of 15 ml/hr.

Solution A had the following composition:
(i) Leucine 52.5 g/l
(ii) Isoleucine 28.5 g/l
(iii) Phenylalanine 37.5 g/l
(iv) Valine 42.5 g/l
(v) Methionine 4.8 g/l
(vi) Other amino acids ≦1.5 g/l
(vii) NaCl 80 g/l This solution was contacted with the following organic phase:
(1) 2-Ethylhexylphosphoric acid 75%
(2) 2-Ethylhexanol 10%
Kerosene 15%

This operation was carried out in the apparatus shown in FIG. 1, in a liquid/liquid extraction battery 5 operating countercurrently and comprising 24 theoretical stages. The solvent was introduced into the battery at stage 1 at a rate of 170 ml/hr. The amino acid solution was introduced at stage 12 at a rate of 40 ml/hr. Selective washing was carried out using a 1.25N hydrochloric acid solution at a rate of 55 ml/hr. 10N sodium hydroxide was introduced at stage 1 at a rate of 10 ml/hr. The depleted aqueous phase C emanating from stage 1 contained more than 99.8% of each of the amino acids valine, methionine and other acids and less than 10 mg/l leucine, isoleucine and phenylalanine, which corresponds to a degree of extraction greater than 99.9% for the three acids.

Solution C had the following composition:
(i) Valine 17.9 g/l
(ii) Methionine 2 g/l
(iii) Other amino acids ≦0.6 g/l
(iv) Leucine <10 ml/l
(v) Isoleucine <10 mg/l
(vi) Phenylalanine <10 mg/l
(vii) NaCl 33 g/l The charged solvent emanating from the battery 5 was circulated into a battery 6 having 3 stages, wherein the amino acids extracted in aqueous phase were recovered by countercurrently contacting the solvent with 2N sulfuric acid at a rate of 40 ml/hr.

The aqueous phase D had the following composition:
(i) Leucine 52.5 g/l
(ii) Isoleucine 28.5 g/l
(iii) Phenylalanine 37.5 g/l
(iv) Other amino acids ≦0.2 g/l This solution was continuously neutralized with 10N sodium hydroxide, at a rate of 8 ml/hr. It then had the following composition:
(i) Leucine 42.7 g/l
(ii) Isoleucine 23.7 g/l
(iii) Phenylalanine 31.7 g/l
(iv) Other amino acids ≦0.2 g/l
(v) Other amino acids 142 g/l Phenylalanine was extracted from this solution by countercurrently contacting same with the following organic phase:
Aliquat®336 15% in the chloride form
Solvesso®150 85%

The contacting was carried out in the apparatus of FIG. 1, in a liquid/liquid extraction battery 7 comprising 16 theoretical stages. The solvent was introduced into the battery at stage 1 at a rate of 140 ml/hr. The amino acid solution was introduced at stage 8 at a rate of 48 ml/hr. Selective washing was carried out using 0.7N sulfuric acid solution at a rate of 26 ml/hr and introduced at stage 16.

10N sodium hydroxide was introduced at stage 1 at a rate of 3 ml/hr. Under these conditions, the phenylalanine extracted was present in the solvent at a purity of 99.9%, with an extraction yield of 99.7%.

The depleted aqueous phase E emanating from stage 1 had the following composition:
(i) Leucine 28.4 g/l
(ii) Isoleucine 15.4 g/l
(iii) Other amino acids ≦0.1 g/l
(iv) $Na_2SO_4$ 92 g/l The solvent charged with phenylalanine emanating from the battery 7 was circulated to a battery 8 having 3 stages, wherein the phenylalanine extracted in aqueous phase was recovered by countercurrently contacting same with a 2N sulfuric acid solution at a rate of 24 ml/hr. An aqueous acid solution of phenylalanine, 87.5 g/l, and containing less than 0.1% of the other amino acids, was produced.

The depleted solution E, principally containing leucine and isoleucine, was circulated to a liquid/liquid extraction battery 9 operating countercurrently and comprising 21 theoretical stages.

The solvent was:
(1) 2-Diethylhexylphosphoric acid 75%
(2) 2-Ethylhexanol 10%
(3) Kerosene 15%
and was introduced into the battery at stage 1 at a rate of 90 ml/hr.

The amino acid solution was introduced at stage 12 at a rate of 74 ml/hr. Selective washing was carried out using an 0.34N sulfuric acid solution, introduced at stage 21 at a rate of 130 ml/hr. 10N sodium hydroxide was introduced at stage 1 at a rate of 4 ml/hr. Under these conditions, the exhausted aqueous phase was an aqueous solution of isoleucine, 5.6 g/l, and having a purity greater than 98.8%.

The solvent charged with leucine was introduced into a liquid/liquid extraction battery 10 operating countercurrently and comprising 3 theoretical stages. The leucine extracted was transferred into aqueous phase by contacting the charged solvent with a 2N hydrochloric acid solution at a rate of 20 ml/hr. An acid aqueous solution of leucine, 105 g/l, and having a plurality of at least 99.8%, was produced.

EXAMPLE 2

The regenerated extract of the first separation of Example 1, designated A, was recovered and continuously neutralized by addition thereto of 10N sodium hydroxide at a rate of 15 ml/hr.

The solution had the following composition:
(i) Valine 42.50 g/l
(ii) Leucine 52.50 g/l
(iii) Isoleucine 28.50 g/l
(iv) Phenylalanine 37.50 g/l
(v) Methionine 4.75 g/l
(vi) Tyrosine 4.75 g/l
(vii) Other amino acids ≦1.50 g/l
(viii) $Na_2S_4$ 142 g/l The phenylalanine was extracted from this solution by continuously countercurrently contacting same with an organic phase of Aliquat®336, in chloride form, at 15% by volume in kerosene.

Figure 2:
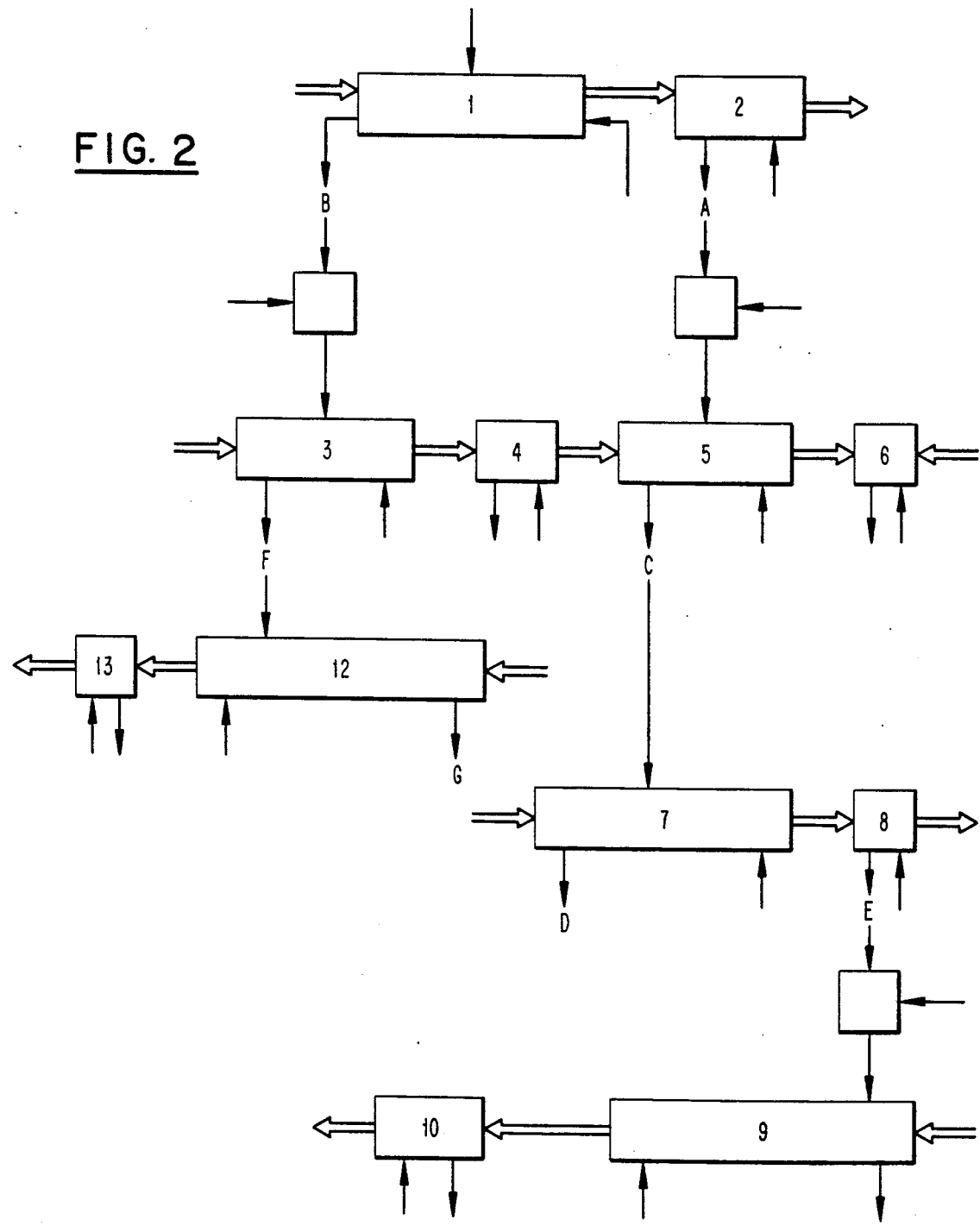
FIG. 2 is a schematic/diagrammatic illustration of another embodiment of apparatus/process according to this invention.

This operation was carried out in the apparatus shown in FIG. 2, in a liquid/liquid extraction battery 5 operating countercurrently and comprising 16 theoretical stages. The solvent was introduced into the battery at stage at a rate of 117 ml/hr. The amino acid solution was introduced at stage 8 at a rate of 40 ml/hr. Selective washing was carried out using an 0.85N sulfuric acid solution at a rate of 22 ml/hr, introduced at stage 16. 10N sodium hydroxide was introduced at stage 1 at a rate of 2.5 ml/hr.

Under these conditions, phenylalanine was present in the solvent in a purity of 99.9% and the extraction yield was equal to 99.7%.

The solvent enriched in phenylalanine and emanating from the battery was introduced into a battery 6 having 3 stages, wherein the phenylalanine was extracted in aqueous phase and recovered by countercurrently contacting the solvent with a 2N sulfuric acid solution at a rate of 20 ml/hr. An aqueous acid solution of 75 g/l phenylalanine, containing less than 0.1% of the other amino acids, was obtained.

The depleted solution C emanating from stage 1 contained:
(i) Leucine 33.9 g/l
(ii) Isoleucine 18.4 g/l
(iii) Valine 27.4 g/l
(iv) Methionine 3.1 g/l
(v) Tyrosine 3.1 g/l
(vi) Other amino acids ≦1 g/l
(vii) $Na_2SO_4$ 142 g/l It was contacted with an organic phase having the following composition:
(1) 2-Diethylhexylphosphoric acid 75%
(2) 2-Ethylhexanol 10%
(3) Kerosene 15%

This operation was carried out in the apparatus shown in FIG. 2, in a liquid/liquid extraction battery 7 operating countercurrently and comprising 21 theoretical stages. The solvent was introduced into the battery at stage at a rate of 218 ml/hr. The amino acid solution was introduced into stage 11 at a rate of 62 ml/hr. Selective washing was carried out using an 0.7N sulfuric acid solution at a rate of 156 ml/hr. 10N sodium hydroxide was introduced at stage 1 at a rate of 13.5 ml/hr.

The depleted aqueous phase D emanating from stage 1 contained more than 99.8% of each of the amino acids valine, methionine, tyrosine and the other amino acids, and less than 10 mg/l leucine and isoleucine, which corresponds to a degree of extraction of these two amino acids of 99.9%.

Solution D had the following composition:
(i) Leucine ≦10 mg/l
(ii) Isoleucine ≦10 mg/l
(iii) Valine 7.8 g/l
(iv) Methionine 0.9 g/l
(v) Tyrosine 0.87 g/l
(vi) Other amino acids ≦0.3 g/l
(vii) $Na_2SO_4$ 40 g/l The charged solvent emanating from battery 7 was introduced into a battery 8 having 3 stages, wherein the extracted amino acids were recovered, principally leucine and isoleucine, by contacting the solvent with a 2N hydrochloric acid solution. After neutralization with 10N sodium hydroxide, this solution E had the following composition:
(i) Leucine 40 g/l
(ii) Isoleucine 28.50 g/l
(iii) Other amino acids ≦0.1 g/l This solution was introduced into an extraction battery 9 operating countercurrently and comprising 21 theoretical stages. The solvent contained:
(1) 2-Diethylhexylphosphoric acid 75%
(2) 2-Ethylhexanol 10%
(3) Kerosene 15%
and was introduced into the battery at stage 1 at a flow rate of 18 ml/l, with the solution of amino acids being introduced into stage 12 at a rate of 40 ml/hr. Selective washing was carried out using 0.5N hydrochloric acid at a rate of 70 ml/hr. 10N sodium hydroxide was introduced at stage 1 at a rate of 1.2 ml/hr. Under these conditions, the depleted aqueous phase was a solution of isoleucine, 10.4 g/l, and having a purity greater than 98.8%.

The charged solvent containing the leucine was countercurrently contacted with a 2N hydrochloric acid solution at a rate of 10 ml/hr, in a battery 10 having 3 theoretical stages. An aqueous acid solution of leucine, 160 g/l, and having a purity of at least 99.8%, was obtained.

EXAMPLE 3

5 ml of a solution, 0.093 molar in L-phenylalanine and 0.052 molar in aspartic acid, produced by transamination at a pH of 7.5, were adjusted to pH 2.9 by the addition of concentrated hydrochloric acid thereto. To this solution, 5 ml of a mixture of bis(2-ethylhexyl)phosphoric acid, 2-ethylhexanol and kerosene, having the following composition by volume, were added:
(1) Bis(2-ethylhexyl)phosphoric acid 75%
(2) 2-Ethylhexanol 10%
(3) Kerosene 15%

The mixture was agitated and two phases separated; the amino acid content of each of the two phases was then determined.

94.2% of the L-phenylalanine present in the initial solution had transferred into the organic phase, while 95% of L-aspartic acid remained in the aqueous phase.

EXAMPLE 4

To 450 ml of the solution of Example 1, adjusted to pH 2.9, 450 ml of a mixture of bis(2-ethylhexyl)phosphoric acid, 2-ethylhexanol and kerosene, having the following composition, were added:
(1) Bis(2-ethylhexyl)phosphoric acid 50%
(2) 2-Ethylhexanol 6.7%
(3) Kerosene 43.3%

The mixture was agitated and, after settling, separated into two phases. The organic phase was back-extracted with an equivalent volume of 2N hydrochloric acid. Determination of L-phenylalanine in the aqueous phases of the first extraction indicated that 87% of the L-phenylalanine had been extracted.

EXAMPLE 5

5 ml of an aqueous solution, 0.05 molar in L-tryptophan, 0.05 molar in L-serine and 0.083 molar in glycine, were adjusted to pH 3 by addition of concentrated HCl. To this solution, 5 ml of a mixture of bis(2-ethylhexyl)phosphoric acid, 2-ethylhexanol and kerosene, having the following composition by volume, were added:
(1) Bis(2-ethylhexyl)phosphoric acid 75%
(2) 2-Ethylhexanol 10%
(3) Kerosene 15%

The mixture was agitated and, after settling, separated into two phases are separated. Analysis of the organic phase evidenced that 96% of L-tryptophan was extracted into the organic phase, with more than 95% of the L-serine and glycine remaining in the aqueous phase.

EXAMPLE 6

5 ml of an aqueous solution, 0.05 molar in L-tryptophan, 0.3 molar in L-serine and 0.75 molar in glycine, were adjusted to pH 3 with concentrated hydrochloric acid. To this solution were added 5 ml of the extractant composition utilized in Example 5.

After agitation and settling, analysis of the aqueous phase evidenced that 97% of L-tryptophane was transferred into the organic phase, and less than 5% of L-serine and glycine were extracted.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the separation of desired amino acids from more complex admixture thereof, comprising selectively countercurrently extracting such desired amino acids from an essentially cystine free solution of a plurality of amino acids into an organic phosphorus acid extractant, or into such phosphorus acid extractant in solution in at least one alcohol, ether, ketone, hydrocarbon, or mixture thereof.

2. The process as defined by claim 1, said admixture of amino acids comprising a natural protein hydrolysate.

3. The process as defined by claim 1, said admixture comprising at least 100 g/l of amino acids.

4. The process as defined by claim 1, said admixture comprising at least 200 g/l of amino acids.

5. The process as defined by claim 1, said extractant comprising an organic phosphorus acid and at least one linear or branched chain aliphatic alcohol containing from 6 to 14 carbon atoms and/or at least one aliphatic hydrocarbon.

6. The process as defined by claim 5, said organic phosphorus acid comprising a dialkylphosphoric, dialkylphosphonic, dialkylphosphinic, diarylphosphoric, diarylphosphonic, or diarylphosphinic acid.

7. The process as defined by claim 6, said organic phosphorus acid comprising 2-ethylhexylphosphoric acid.

8. The process as defined by claim 5, said extractant comprising at least one linear or branched chain aliphatic alcohol containing from 8 to 10 carbon atoms.

9. The process as defined by claim 8, said aliphatic alcohol comprising 2-ethylhexanol.

10. The process as defined in claim 5, said extractant comprising kerosene.

11. The process as defined in claim 5, said extractant having the following composition, by volume:
2-diethylhexylphophoric acid: 40-80%
2-ethylhexanol: 5-20%
kerosene: 55-0%

12. The process as defined in claim 1, further comprising selectively countercurrently back-extracting desired individual amino acids from the organic phase of extraction.

13. The process as defined by claim 1, further comprising selectively countercurrently back-extracting desired individual amino acids from the aqueous phase of extraction.

* * * * *